United States Patent [19]

Liou et al.

[11] Patent Number: 5,780,662

[45] Date of Patent: Jul. 14, 1998

[54] NAPHTHYL AND ETHER CHAIN-CONTAINING CARBOXYL DERIVATIVES

[75] Inventors: Guey-Sheng Liou, Hsinchu; Sheng-Huei Hsiao; Jen-Chang Yang, both of Taipei, all of Taiwan

[73] Assignee: Industrial Technology Research Institute, Taipei, Taiwan

[21] Appl. No.: 936,686

[22] Filed: Sep. 24, 1997

Related U.S. Application Data

[62] Division of Ser. No. 702,388, Aug. 14, 1996, Pat. No. 5,712,409.

[30] Foreign Application Priority Data

Jun. 27, 1996 [TW] Taiwan .................................. 85107751

[51] Int. Cl.⁶ .................................................. C07C 255/04
[52] U.S. Cl. .................................................. 558/420
[58] Field of Search .................................................. 558/420

[56] References Cited

U.S. PATENT DOCUMENTS

| | | | |
|---|---|---|---|
| 5,268,487 | 12/1993 | Yang et al. | 548/456 |
| 5,340,904 | 8/1994 | Yang et al. | 528/185 |
| 5,414,070 | 5/1995 | Yang et al. | 528/310 |

*Primary Examiner*—Joseph McKane
*Assistant Examiner*—Ebenezer Sackey
*Attorney, Agent, or Firm*—Sughrue, Mion, Zinn, Macpeak & Seas, PLLC

[57] ABSTRACT

New aromatic dicarboxylic acids, 1,4- or 2,6-Bis(p-carboxyphenoxy)naphthyl is prepared by the reaction of p-fluorobenzonitrile with 1,4-naphthalenediol, followed by hydrolysis. Wholly aromatic polyamides having superior solubility in a variety of organic solvents and have good thermal stability can be obtained by reacting the new aromatic dicarboxylic acids with aromatic diamines. Transparent, tough and flexible films of these polyamides can be cast from the solutions thereof and these polyamides are easily processable high-performance polymer materials.

3 Claims, No Drawings

NAPHTHYL AND ETHER CHAIN-CONTAINING CARBOXYL DERIVATIVES

This is a divisional of application Ser. No. 08/702,388 filed Aug. 14, 1996 now U.S. Pat. No. 5,712,409.

BACKGROUND OF THE INVENTION

The present invention relates to naphthyl and ether chain-containing carboxyl derivatives and method for preparing the same. The carboxyl derivatives can be used to prepare wholly aromatic polyamides which are readily soluble in various organic solvents and have good thermal stability.

Wholly aromatic polyamides (aramides) are characterized as highly thermal stable polymers with a favorable balance of physical and chemical properties. However, these polymers are generally intractable and lack the properties essential for successful fabrication into useful forms such as films and fibers due to their high melting or glass transition temperature and their limited solubility in organic solvents. For example, polyamides or polyimides having the structures indicated below generally have high glass transition temperatures ($T_g$) and melting points ($T_m$), and accordingly can not easily be fabricated into films or fibers.

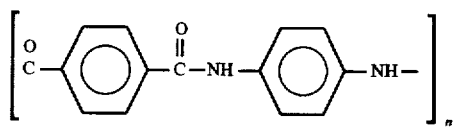

(Kevlar)
Tm = 500° C.

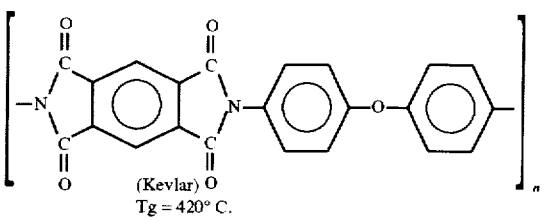

(Kevlar)
Tg = 420° C.

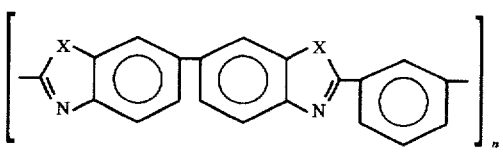

X:O (Polybenzoxazole)
Tg = 370° C.

X:S (Polybenzothiazole)
Tg = 425° C.

X:NH (Polybenzimidazole)

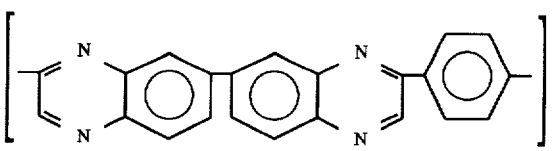

Polyquinoxaline
Tg = 397° C.

Some melt processable linear polyimides having structures indicated below have been developed.

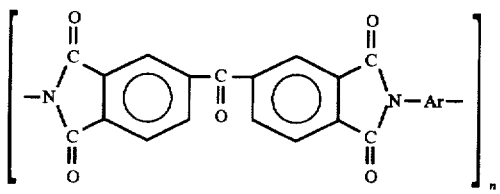

PI 2080  Tg:310° C.

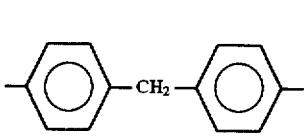

(20%)  (80%)

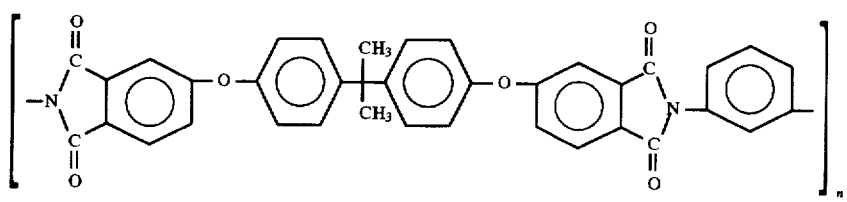

Ultem  Tg:216° C.

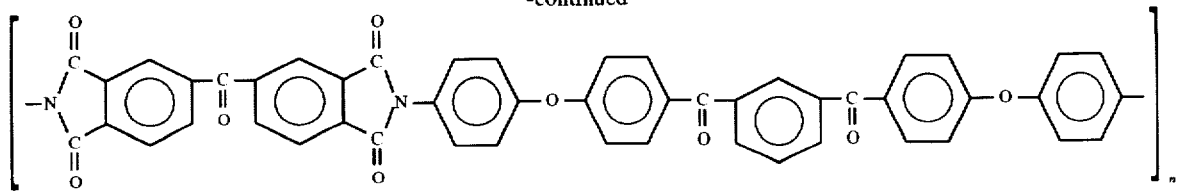

LARC-CPI      Tg:222° C.

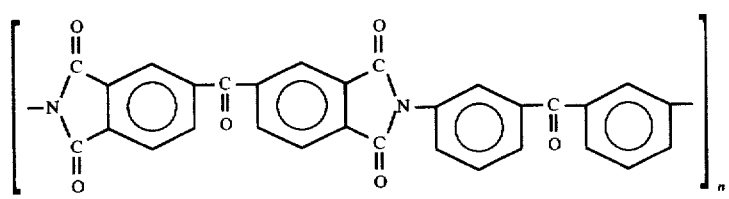

LARC-TPI      Tg:264° C.

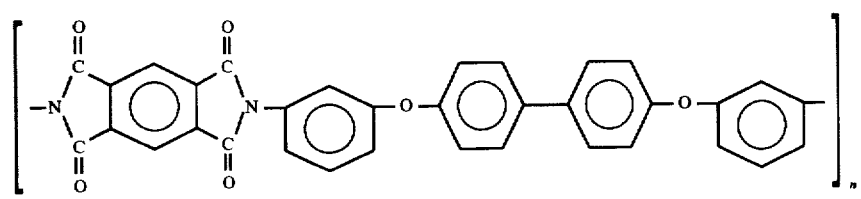

New-TPI      Tg:270° C.

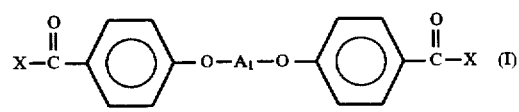

These polyimides have superior thermal stability, chemical resistance, dimension stability, mechanical properties and electrical properties. However, their solubility in organic solvents is still low and accordingly they are not suitable for being fabricated into films or fibers.

SUMMARY OF THE INVENTION

It is therefore an object of the invention to provide a raw material which can be used to react with aromatic diamines to prepare wholly aromatic polyamides having good solubility in various organic solvents and good thermal stability.

It has been found by the inventors that reacting 1,4-naphthyl or 2,6-naphthyl-containing diacids or their derivatives of the formula (I) with aromatic diamines can attain the object of the invention:

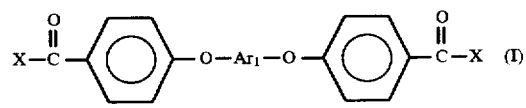

wherein X represents CL, OH or OR wherein R is a $C_1$–$C_6$ alkyl and $Ar_1$ represents:

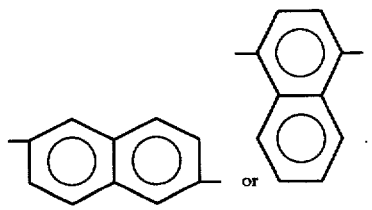

Compounds of formula (I) can be prepared by subjecting 1,4- or 2,6-naphthalenediol and p-fluorobensonitrile to nucleophilic fluoro-displacement reaction to obtain a compound of formual (II):

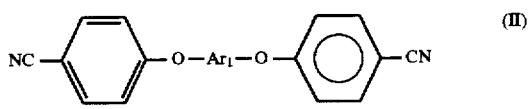

wherein $Ar_1$ represents:

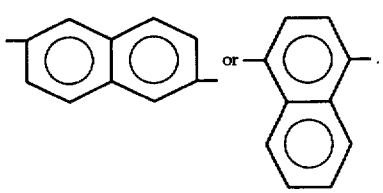

followed by hydrolysis, esterification or chlorination.

Examples of preparing the naphthyl and ether chain-containing carboxyl compounds are depicted in the following reaction schemes.

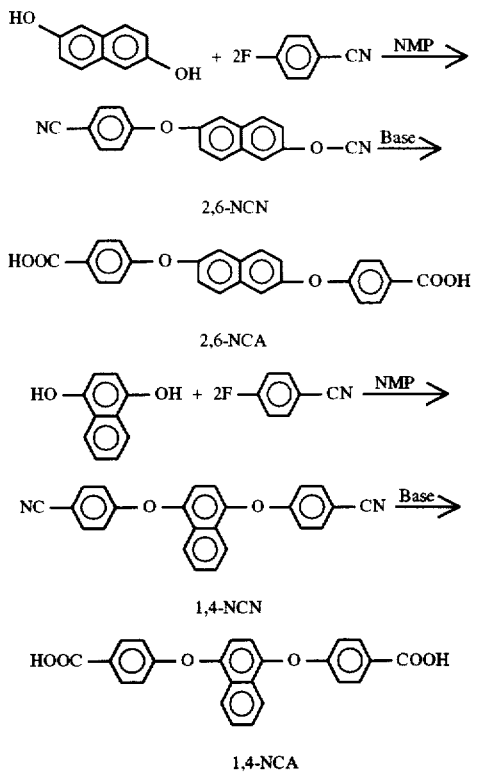

The present invention is more specifically described by the following non-limiting examples.

EXAMPLE 1

Preparation of 1,4-Bis(p-carboxylphenoxy)naphthyl (1,4-NCA)

In a three-neck flask fitted with a nitrogen inlet, a Dean-StarK trap and a condenser, were placed 16.02 g (100 mmole) of 1,4-naphthalenediol and 27.64 g (200 mmole) with 100 mL of toluene and 200 mL of NMP. The mixture was heated and stirred at 140° C. for 6 hours under nitrogen to facilitate dehydration. After the toluene was removed, the mixture was cooled and then 24.22 g (200 mmol) of p-fluorobenxonitrile was added. The reaction was carried out at 170° C. for 10 hours and then the reaction mixture was allowed to cool and poured into 3 L of cool water. The product as filtrated and recrystallized from acetonitrile to provide 21.75 g (60% yield) of 1,4-Bis(p-cyanophenoxy)naphthyl (1,4-NCN) in white needles, mp 197°–198° C. The IR spectrum (KBr) exhibited absorption (C≡N) at 2228 cm$^{-1}$ and (C—O—C) at 1108 and 1236 cm$^{-1}$. ANAL. Calcd. for $C_{24}H_{14}N_2O_2$: C, 79.54%; H, 3.89%; N, 7.73%; Found: C, 79.26%; H,4.08%; N, 7.61%.

The obtained 1,4-NCN was then hydrolyzed in potassium hydroxide solution until no further ammonia was generated. The solution was cooled, and the pH value was adjusted by hydrochloric acid to near 3. A white precipitate of 1,4-NCA was formed and collected by filtrating and drying under vacuum. The yield was 100%. The melting point of the obtained white powder was 354°–355° C. without purification. The IR spectrum (KBr) exhibited an absorption at 1680 cm$^{-1}$ (C=O).

EXAMPLE 2

Preparation of 2,6-Bis(p-carboxylphenoxy)naphthyl (2,6-NCA)

In a three-neck flask fitted with a nitrogen inlet, a Dean-StarK trap and a condenser, were placed 16.02 g (100 mmole) of 2,6-naphthalenediol and 27.64 g (200 mmole) with 100 mL of toluene and 200 mL of NMP. The mixture was heated and stirred at 140° C. for 6 hours under nitrogen to facilitate dehydration. After the toluene had been removed, the mixture was cooled and then 24.22 g (200 mmol) of p-fluorobenxonitrile was added. The reaction was carried out at 170° C. for 10 hours and then the reaction mixture was allowed to cool and poured into 3 L of cool water. The product was filtrated and recrystallized from acetonitrile to provide 21.75 g (60% yield) of 2,6-Bis(p-cyanophenoxy)naphthyl (2,6-NCN) in white needles, mp 252.2° C. The IR spectrum. (KBr) exhibited absorption (C≡N) at 2228 cm$^{-1}$ and (C—O—C) at 1108 and 1236 cm$^{-1}$. ANAL. Calcd. for $C_{24}H_{14}N_2O_2$: C, 79.54%; H, 3.89%; N, 7.73%; Found: C, 79.26%; H.4.08%; N, 7.61%.

The obtained 2,6-NCN was then hydrolyzed in potassium hydroxide solution until no further ammonia was generated. The solution was cooled, and the pH value was adjusted by hydrochloric acid to near 3. A white precipitate of 2,6-NCA was formed and was collected by filtrating and drying under vacuum. The yield was 100%. The melting point of the obtained white powder was 352.3° C. without purification. The IR spectrum (Kbr) exhibited an absorption at 1680 cm$^{-1}$ (C=O).

The 1,4-NCA and 2,6-NCA obtained from examples 1 and 2 can be reacted with aromatic diamines to produce wholly aromatic polyamides of superior organic solubility and thermal stability. In the following applied examples, suitable aromatic diamines used in the present invention have the following formula:

wherein $Ar_2$ represents aromatic radicals such as the following:

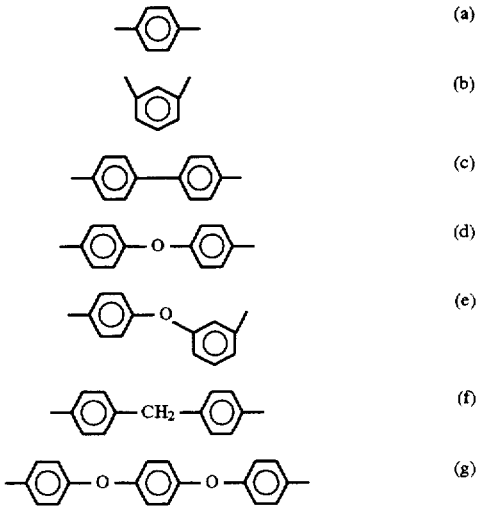

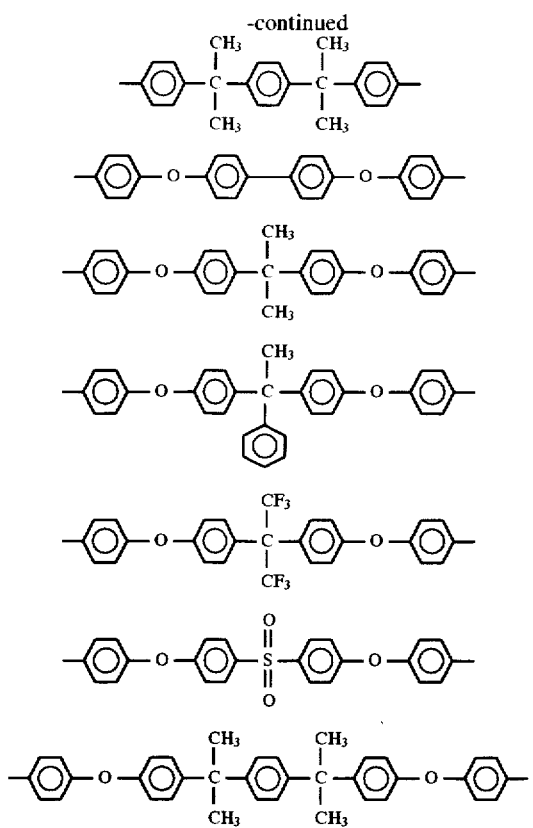

That is, the above, aromatic diamines are p-Phenylenediamine (3a), m-phenylenediamine (3b), benzidine (3c), 4,4'oxydianiline (3d), 3,4'-oxydianiline (3e), 4,4'-diaminodiphenyl methane (3f), 1,4-bis(p-aminophenoxy) benzene (3g), α, α-bis (p-aminophenyl) -1,4-diisopropylbenzene (3h), 4,4'-bis(p-aminophenoxy) biphenyl (3i), 2,2'-bis|p-(p-aminophenoxy)phenylpropane (3j), 1,1'-bis[p-(p-aminophenoxy)phenyl]-1-phenylethane (3k), 2,2'-bis|p-(p-aminophenoxy)phenyl| hexafluoropropane (3l), bis[p-(p-aminophenoxyOphenyl] sulfone (3m), and α, α-bis|p-(p-aminophenoxy)1,4-diisopropylbenzene (3n). Note that according to the present invention, diamines, (3a) and (3b)should be purified by distillation before use while diamines (3c), (3d), (3e) (3f) and (3g) can be used as received. Diamines (3h), (3i), (3j), (3k) (3l), (3m) and (3n) are prepared by aromatic nucleophilic substitution reaction of the corresponding bisphenols and p-chloronitrobenzene in the presence of potassium carbonate, yilding dinitro compounds and subsequent reduction using hydrazine as reducing agent and palladium as catalyst (K. Suematsu, Micromolecules, 18, 2083 (1985).

APPLIED EXAMPLE 1

Preparation of Wholly Aromatic Polyamide (5d) of the Invention

A mixture of 0.25 g (1.25 mmole) of 4,4'-oxydianiline (4d), 0.50 g (1.25 mmole) of 1,4-NCA (prepared from preparative Example 1), 0.5 g of calcium chloride, 5 ml of NMP, 1 mL of pyridine, and 0.9 mL of triphenyl phosphite was heated at 100° C. for 3 hours. The obtained polymer solution was trickled into 300 mL of methanol, collected by filtration and dried at 100° C. under vacuum. The inherent viscosity of the polymer obtained was 2.22 dL/g, measured at a concentration of 0.5 g/dL in DMAc containing 5 wt % LiCL at 30° C. The $T_g$ was 240° C. measured from the second heating trace of DSC conducted at a heating rate of 20° C./min in $N_2$. Other properties are described in Table 2

APPLIED EXAMPLES 2-14

Preparations of Wholly Aromatic Polyamides 5a–5c and 5e–5n of the Invention

The same procedures of applied Example 1 were followed except that aromatic diamines 4a–4c and 4e–4n were used. The inherent viscosities $\eta_{inh}$ and $T_g$ obtained polymers were measured and shown in Table 1.

TABLE 1

| NO. | $\eta_{inh}$ (dl/g) | $T_g$ (°C.) |
|---|---|---|
| 5a | 1.40 | — |
| 5b | 1.34 | 204 |
| 5c | 1.68 | — |
| 5d | 2.22 | 240 |
| 5e | 1.42 | 233 |
| 5d | 1.40 | 220 |
| 5g | 1.52 | 220 |
| 5h | 1.28 | 145 |
| 5I | 1.30 | 213 |
| 5j | 1.86 | 213 |
| 5k | 1.32 | 227 |
| 5l | 1.58 | 216 |
| 5m | 1.27 | 220 |
| 5n | 1.70 | 213 |

In addition, the solubilities and tensile properties of the polymers obtained from Example 1–14 were measured and shown in Table 2 below.

TABLE 2

| polymer code. | Solubility[a] Solvent | | | | | | Tensile Properties[b] | | |
|---|---|---|---|---|---|---|---|---|---|
| | NMP | DMAc | DMF | DMSO | m– | THF | Tensile strength (MPa) | Elongation to break (%) | Tensile modulus (GPa) |
| 5a | – | – | – | – | – | – | —[c] | — | — |
| 5b | + | + | + | + | + | – | 84 | 10 | 1.91 |
| 5c | – | – | – | – | – | – | —[c] | — | — |
| 5d | + | + | + | + | + | – | —[c] | — | — |
| 5e | + | + | + | + | + | – | 82 | 8 | 1.72 |
| 5f | + | + | + | + | + | – | 64 | 8 | 1.38 |
| 5g | + | ± | – | – | – | – | .86 | 8 | 1.90 |
| 5h | + | + | ± | s | + | s | 83 | 9 | 1.61 |

TABLE 2-continued

| polymer code | Solubility[a] Solvent | | | | | | Tensile Properties[b] | | |
|---|---|---|---|---|---|---|---|---|---|
| | NMP | DMAc | DMF | DMSO | m-THF | | Tensile strength (MPa) | Elongation to break (%) | Tensile modulus (GPa) |
| 5i | + | + | – | – | – | – | 73 | 7 | 1.64 |
| 5j | + | + | ± | ± | + | s | 104 | 9 | 2.14 |
| 5k | + | + | s | s | + | +h | 70 | 7 | 1.64 |
| 5l | + | + | + | + | + | + | 71 | 8 | 1.52 |
| 5m | + | + | s | s | + | + | 74 | 8 | 1.66 |
| 5n | + | + | +h | +h | + | s | 65 | 6 | 1.54 |

[a]+: soluble, +h: soluble on heating, ±: partially soluble, s: swelling, –: insoluble
[b]Films were cast from slow evaporation of polymer solution in DMAc.
[c]No available samples could be obtained.

APPLIED EXAMPLE 15

Preparation of Wholly Aromatic Polyamide (4d) of the Invention

A mixture of 0.25 g (1.25 mmole) of 4,4'-oxydianiline (4d), 0.50 g (1.25 mmole) of 2,6-NCA (prepared from Example 2), 0.5 g of calcium chloride, 5 ml of NMP, 1 mL of pyridine, and 0.9 mL of triphenyl phosphite was heated at 100° C. for 3 hours. The obtained polymer solution was trickled into 300 mL of methanol, collected by filtration and dried at 100° C. under vacuum. The inherent viscosity, $T_g$ and tensile properties of the polymer (4d) obtained were measured and described in Table 3 and Table 4.

APPLIED EXAMPLES 16–29

Preparations of Wholly Aromatic Polyamides 4a–4c and 4e–4n of the Invention

The same procedures of Applied Example 15 were followed except that aromatic diamines 4a–4c and 4e–4n were used. The inherent viscosities $\eta_{inh}$ and $T_g$ and tensile properties of the obtained polymers were measured and shown in Table 3 and Table 4.

TABLE 3

| | | | | $\eta_{inh}$[d] (dl/g) | |
|---|---|---|---|---|---|
| No. | NMP (ml) | Py (ml) | CaCl$_2$ (g) | in DMAc-5% LiCl | in H$_2$SO$_4$[1] |
| 4a | 10 | 2.5 | 0.6 (+0.6 gLiCl) | 1.43 | 1.34 |
| 4b | 5 | 1.3 | 0.6 | 0.31 | 1.27 |
| 4c | 10 + 5[b] | 2.5 | 0.9 | —[e] | 0.64 |
| 4d | 4 + 4[c] | 1.0 | 0.5 | 2.19 | 1.80 |
| 4e | 4 | 1.0 | 0.5 | 1.50 | 0.73 |
| 4f | 4 + 2[c] | 1.0 | 0.5 | 1.47 | 1.22 |
| 4g | 5 + 2[c] | 1.3 | 0.6 | 1.56 | 1.43 |
| 4h | 5 | 1.3 | 0.6 | 1.30 | 0.07 |
| 4i | 5 + 15[b] | 1.3 | 0.6 (+0.5 gLiCl) | —[e] | 1.34 |
| 4j | 5 | 1.3 | 0.6 | 1.64 | 0.06 |
| 4k | 5 + 2[c] | 1.3 | 0.6 | 1.39 | 0.10 |
| 4l | 5 + 4[c] | 1.3 | 0.6 | 1.72 | 1.71 |
| 4m | 5 + 2[c] | 1.3 | 0.6 | 1.39 | 1.53 |
| 4n | 5 + 4[c] | 1.3 | 0.6 | 1.71 | 0.06 |

[a]Amount of each diacid and diamine monomer = 1.25 mmole, TPP = 0.9 ml (2.5 mmole), reaction temperature = 110° C., reaction time = 3 hr.
[b]The polymer precipitated during the reaction and could not be redissolved by further addition of NMP.
[c]An initial amount of NMP was used and an additional amount of NMP was supplemented when the reaction was too viscous to stir.
[d]Measured at a concentration of 0.5 g/dl at 30° C.
[e]Insoluble
[f]Determined as soon as the solid was dissolved completely at room temperature.

TABLE 4

| Polymer code | Tensile properties of polyamide films[a] | | | DSC data | |
|---|---|---|---|---|---|
| | Tensile strength (MPa) | Elongation to break (%) | Tensile modulus (GPa) | $T_g$[b] (°C.) | $T_m$[c] (°C.) |
| 4a | —[d] | — | — | 222 | 465 |
| 4b | 91 | 6 | 2.23 | 218 | 364 |
| 4c | —[d] | — | — | 295 | |
| 4d | —[d] | — | — | 230 | 430 |
| 4e | 88 | 9 | 2.30 | 195 | 267 |
| 4f | 90 | 28 | 2.16 | 247 | 420 |
| 4g | —[d] | — | — | 222 | 423 |
| 4h | 80 | 8 | 2.12 | 205 | |
| 4i | —[d] | — | — | 265 | 438 |
| 4j | 74 | 11 | 1.03 | 216 | |
| 4k | 74 | 17 | 1.35 | 208 | |
| 4l | 70 | 21 | 1.75 | 203 | |
| 4m | 72 | 16 | 1.78 | 235 | |
| 4n | 82 | 10 | 1.93 | 197 | |

[a]Films were cast by slow evaporation of polymer solutions in DMAc.
[b]Temperatures at the midpoint of 20° C./min in nitrogen.
[c]Sharp endotherms appeared in the first DSC heating traces before 480° C.
[d]No available specimens could be obtained.

As can be seen from Tables 1–4, aramids of the present invention are successfully obtained in almost quantitative yield with inherent viscosities of 1.27–2.22 DL/g, and all the molecular weight of these polymers are sufficiently high to permit casting tough and flexible films. In addtion, the solubility behavior of these aramids are highly soluble in polar solvents such as DMAc, NMP, m-cresol and even in less polar pyridine. The glass transition temperatures (Tg) of these polymers are observed to be in the range of 195°–240° C., depending on the structure of diamines component, and decreased with decreasing rigidity and symmetry of the polymer backbone. All these polymers are stable up to 400° C. in both air and nitrogen atmospheres, and the temperatures at 10% weight loss are above 480° C. on the TG curves. The solution cast films of these polymers from NMP solutions have superior crystallinity and mechanical properties.

What is claimed is:

1. A compound of the formula (II):

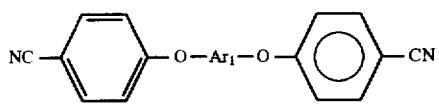
(II)

wherein $Ar_1$ represents:

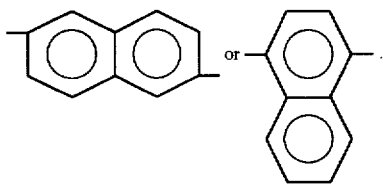

2. The compound of claim 1, which is 1,4-Bis(p-cyanophenoxy)naphthyl.

3. The compound of claim 1, which is 2,6-Bis(p-cyanophenoxy)naphthyl.

* * * * *